United States Patent [19]

Klapper et al.

[11] Patent Number: 5,564,920
[45] Date of Patent: Oct. 15, 1996

[54] PALATAL EXPANDER

[76] Inventors: Lewis Klapper, 744 Falls Cir., Lake Forest, Ill. 60045; Richard W. George, 930 Burridge Ct., Libertyville, Ill. 60048

[21] Appl. No.: 316,884

[22] Filed: Oct. 3, 1994

Related U.S. Application Data

[63] Continuation of Ser. No. 147,950, Nov. 4, 1993, abandoned, which is a continuation-in-part of Ser. No. 57,539, May 6, 1993, abandoned.

[51] Int. Cl.$^6$ ................................................ A61C 7/00
[52] U.S. Cl. ................................................ 433/7
[58] Field of Search ................................................ 433/7

[56] References Cited

U.S. PATENT DOCUMENTS

| | | | |
|---|---|---|---|
| 3,284,902 | 11/1966 | Dillberg et al. | 433/7 |
| 3,832,778 | 9/1974 | Wallshein . | |
| 3,921,294 | 11/1975 | Wallshein . | |
| 3,977,082 | 8/1976 | Siatkowski . | |
| 4,026,023 | 5/1977 | Fisher . | |
| 4,107,843 | 8/1978 | Spino et al. . | |
| 4,144,643 | 9/1979 | Krygier . | |
| 4,197,644 | 4/1980 | Ackerman, Jr. | 433/7 |
| 4,323,345 | 4/1982 | Wallshein . | |
| 4,324,036 | 4/1982 | Reilly | 29/437 |
| 4,354,832 | 10/1982 | Wallshein | 433/7 |
| 4,482,318 | 11/1984 | Forster | 433/7 |
| 4,483,674 | 11/1984 | Schutz | 433/22 |
| 4,571,177 | 2/1986 | Dahan | 433/7 |
| 4,573,914 | 3/1986 | Nord | 433/18 |
| 5,002,485 | 3/1991 | Aagesen | 433/7 |
| 5,266,028 | 11/1993 | Adkisson | 433/18 |

FOREIGN PATENT DOCUMENTS

| | | | |
|---|---|---|---|
| 3728759 | 3/1989 | Germany | 433/7 |
| 659297 | 10/1951 | United Kingdom | 433/7 |

OTHER PUBLICATIONS

American Orthodontics catalog, 1989, p. 38.

*Primary Examiner*—Cary E. O'Connor
*Attorney, Agent, or Firm*—Lloyd L. Zickert

[57] ABSTRACT

A palatal expander which is used for expanding the upper jaw and for moving the maxillary teeth including a rotatable adjusting member and inner and outer expansion members. The adjusting member has an outer sleeve and an inner sleeve disposed partially within the outer sleeve. The expansion members are telescopically and threadedly received by the adjustable member whereby selective rotation of the adjusting member causes the outer and inner expansion members to move away from or toward each other.

33 Claims, 3 Drawing Sheets

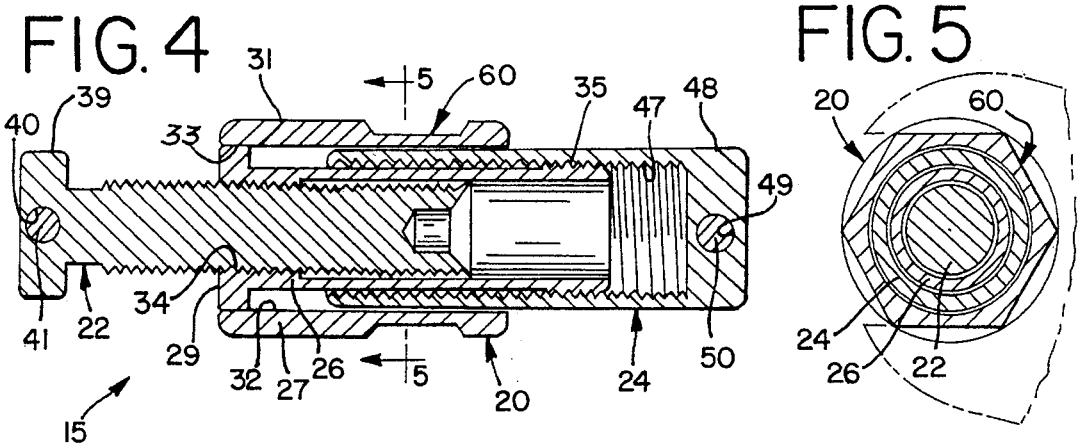
FIG. 4
FIG. 5
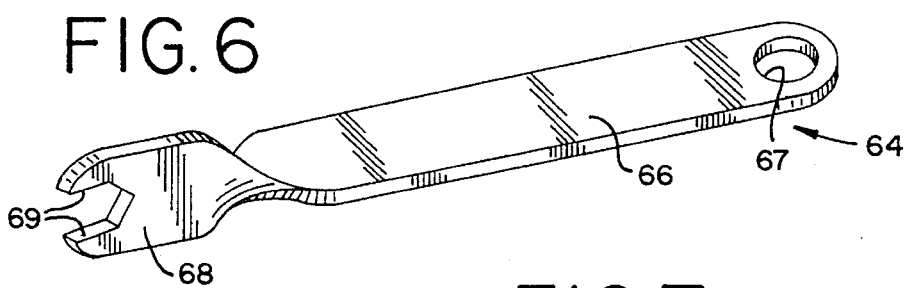
FIG. 6
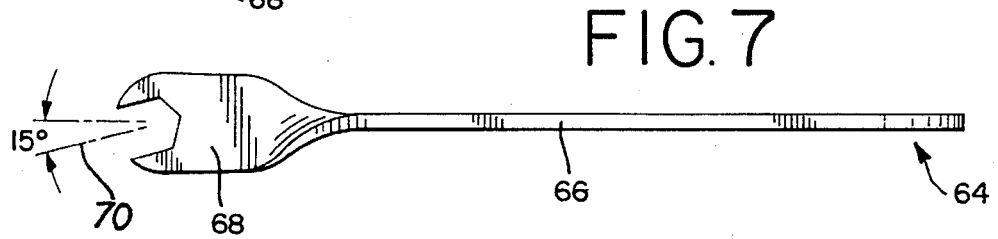
FIG. 7
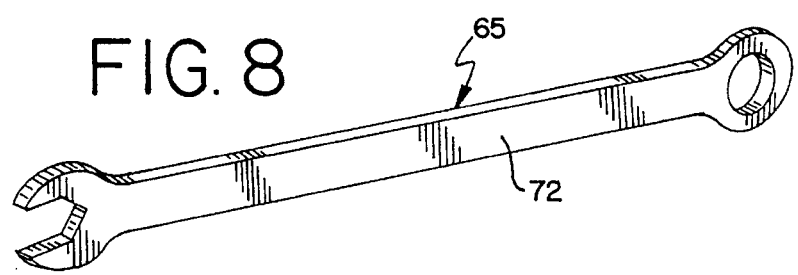
FIG. 8
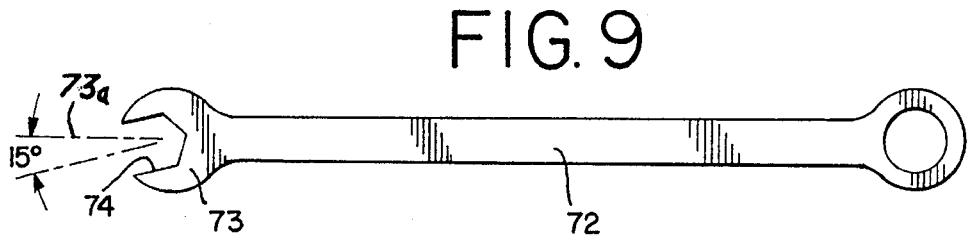
FIG. 9

PALATAL EXPANDER

This application is a continuation of application Ser. No. 08/147,950, filed Nov. 4, 1993, now abandoned, which is a continuation-in-part of our application Ser. No. 08/057,539, May 6, 1993, now abandoned.

This invention relates in general to an orthodontic device, and more particularly to a compact palatal expander or expansion screw for expanding the upper jaw or maxilla and for correcting the position of maxillary teeth to establish proper occlusion with the mandibular teeth.

BACKGROUND OF THE INVENTION

Heretofore, it has been well known in the orthodontic industry to use orthodontic spreaders or expansion screws for expanding the upper jaw and for correcting the position of maxillary teeth. Examples of such devices are disclosed in U.S. Pat. Nos. 3,284,902; 4,197,644; 4,323,345; 4,324,036; 4,354,832, and 4,482,318. While these devices generally perform their intended function, several difficulties have been encountered with such devices.

One difficulty with these devices is that they require adjustment by inserting a small pin type key into a pin hole of a central spindle or actuating portion at the back of the mouth. The pin is then actuated by rotating it posteriorly through a 90-degree arc and removing it in a direction toward the patient's throat. In addition to the difficulty in inserting the pin in the pin hole, these pins can be quite hazardous because they can easily be dropped in the patient's mouth and swallowed by the patient.

Other difficulties with this pin and spindle adjustment system arise because it only allows a one quarter turn per activation and it is difficult to determine if a constant rate of expansion on both sides of the jaw is provided. Similarly, some of these devices are generally not predictable as to the exact amount of expansion created by each activation.

Prior expansion screws have also included guide pins which take up space and restrict access for ease of adjustability. Also, prior expansion screws, such as the embodiment of FIG. 23 in U.S. Pat. No. 4,323,345 and the devices in U.S. Pat. Nos. 4,324,036 and 4,354,832, relied on swedged parts between a screw and threaded tubing to activate the second stage of expansion, and this arrangement frequently failed, resulting in passive screw rotation without activating the second stage, and an inconsistent expansion rate.

Another problem with these devices is that the width of these devices inhibits their usefulness in the palatal cavity of a narrow mouth such as that of a child who has a severe transverse constriction of the maxillary jaw. This problem is multiplied because the narrower the jaw, the more the expansion is necessary, yet the smaller the space that is available for the spreader doing the expansion.

Other prior expansion screws embodied differing thread pitch on the screws and housing which produced a varied rate of expansion per turn over the entire range of activation. Guide pins are required because of perforations in the central spindle to allow insertion of the activating pin, which weakens the spindle structurally.

SUMMARY OF THE INVENTION

The orthodontic appliance of the present invention serves to expand the maxilla or upper jaw in patients who suffer from abnormal lateral growth. More particularly, the palatal expander of the invention orthopedically expands the bony halves of the upper jaw so that the upper teeth can be arranged to properly fit the teeth of the lower jaw.

The present invention overcomes heretofore encountered problems in providing a compact palatal expander or expansion screw which yields a constant rate of expansion over its entire range of activation. The expander of the invention provides two millimeters of expansion for every millimeter of working thread in the expander. Further, the palatal expander of the present invention includes a minimum number of parts in providing a rotatable adjusting member, an inner or first expansion member, and an outer or second expansion member.

The adjusting member includes an outer sleeve with wrench faces on its outer surface and an inner sleeve disposed at least partially within the outer sleeve. The inner sleeve has an exterior screw-threaded surface and an interior screw-threaded surface. The outer expansion member is threadedly received on one end of the adjusting member by the exterior screw-threaded surface of the inner sleeve. The inner expansion member is threadedly received in the other end of the adjusting member by the interior screw-threaded surface of the inner sleeve. The screw-threads of the members are suitably arranged such that rotation of the adjusting member causes the outer and inner expansion members to move away from or toward each other at a consistent rate. In another embodiment, the outer expansion member may be threadedly received by the outer sleeve having an interior screw-threaded surface instead of by the inner sleeve exterior screw-threaded surface. In this embodiment, the exterior surface of the inner sleeve is smooth and provided with markings to measure expansion.

The outer and inner expansion members each include an opening or openings at one end for receiving one or more wires or attachment means for mounting the appliance in the palatal cavity between the sides of the upper jaw. Each wire is respectively attached on one side of the mouth and therefore on opposite sides of the jaw. As the adjusting member is rotated by a wrench inserted at the front of the mouth to engage the wrench faces on the adjusting member, both outer and inner members expand or contract to produce a force that is transferred to the teeth and jaw.

It is therefore an object of the present invention to provide a new and improved palatal expander for expanding or contracting the upper jaw and for correcting the position of maxillary teeth.

A further object of the invention is to provide a new and improved expansion screw having a minimum number of parts and an overall compact profile that occupies a minimum of space transversely.

Another object of the present invention is to provide a palatal expander having positive engagement of all threaded parts during actuation which produces a constant rate of expansion over its entire range of activation.

A further object of the present invention is to provide a new and improved expansion screw having a hex nut adjusting member which allows one-sixth of a turn for finer adjustment and minimizes the insertion distance into the mouth by the wrench and eliminates the need for wrench placement in the back of the mouth.

Another object of the present invention is to provide a compact screw-operated palatal expander which provides two millimeters of expansion for every millimeter of working thread of the expander.

Still another object of the invention is to provide a new and improved expansion screw that eliminates the need of guide pins, thereby facilitating activation access and reducing space requirements.

Another object of the present invention is to provide a compact palatal expander which provides enough expansion to meet clinical needs without being too large for use in very narrow palatal cavities.

Another object of the present invention is to provide a palatal expander which can be easily adjusted with a wrench.

Other objects, features and advantages of the invention will be apparent from the following detailed disclosure, taken in conjunction with the accompanying sheet of drawings, wherein like reference numerals refer to like parts.

DESCRIPTION OF THE DRAWINGS

FIG. 4 is an enlarged longitudinal sectional view of the assembled palatal expander taken substantially along line 4–4 of FIG. 1;

FIG. 5 is a vertical sectional view of the palatal expander taken substantially along line 5—5 of FIG. 4;

FIG. 6 is a perspective view of a wrench used to adjust the palatal expander of the present invention;

FIG. 7 is an elevational view of the wrench of FIG. 6;

FIG. 8 is a perspective view of a modified wrench used to adjust the palatal expander of the present invention;

FIG. 9 is an elevational view of the modified wrench of FIG. 8;

DESCRIPTION OF THE INVENTION

Figure 1:
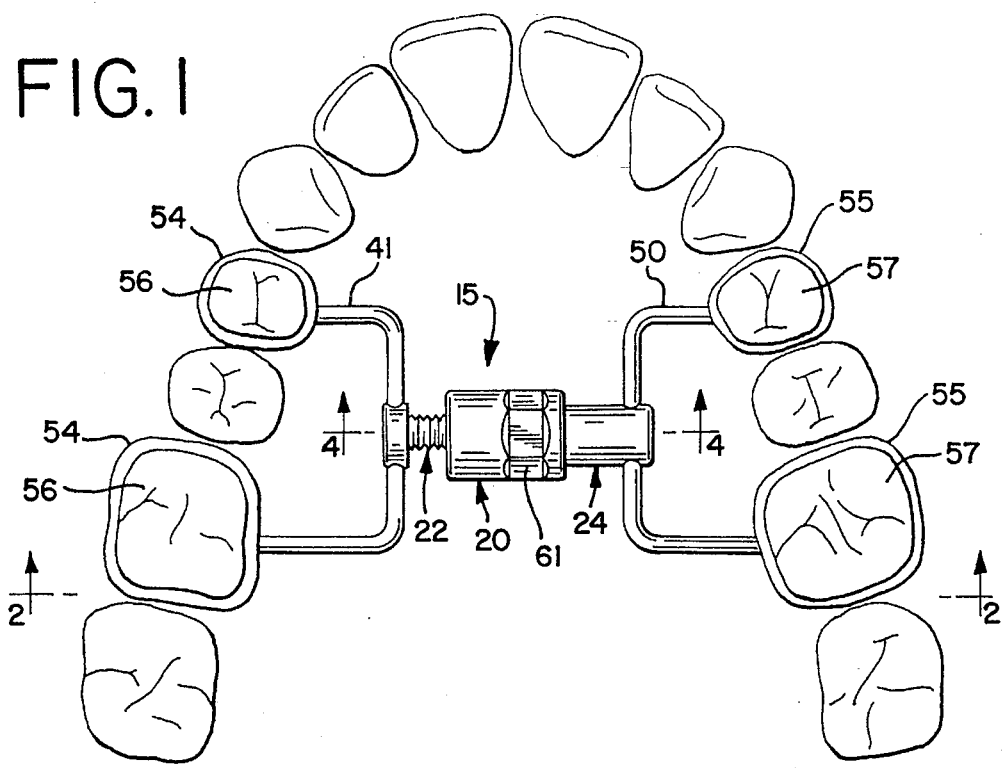
FIG. 1 is a bottom plan view of the maxillary teeth illustrating the palatal expander of the present invention positioned between the maxillary teeth.
Figure 2:
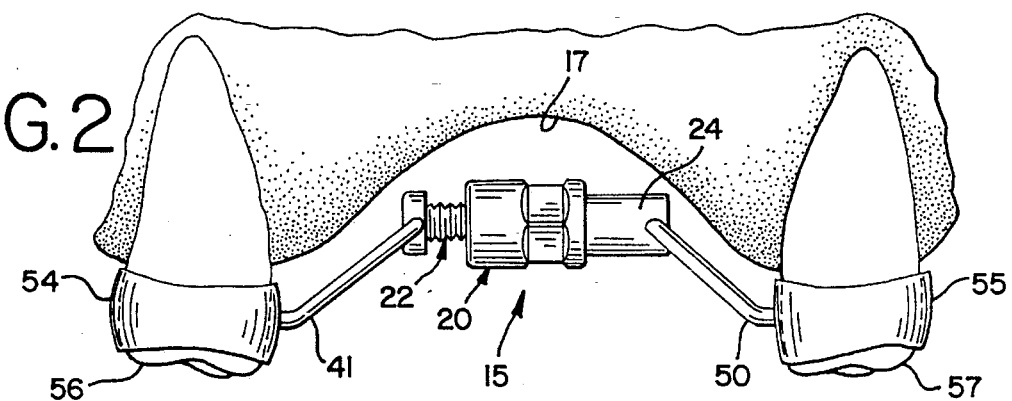
FIG. 2 is an elevational view of the maxillary teeth showing the palatal expander in the palatal cavity of the upper jaw and taken generally along line 2—2 of FIG. 1.
Figure 3:
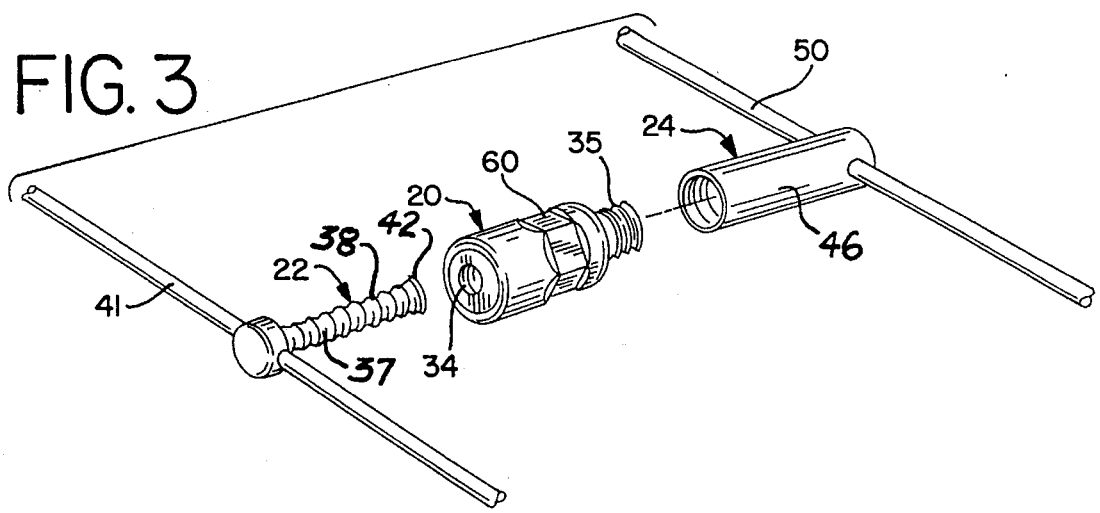
FIG. 3 is an exploded perspective view of the palatal expander.
Figure 10:
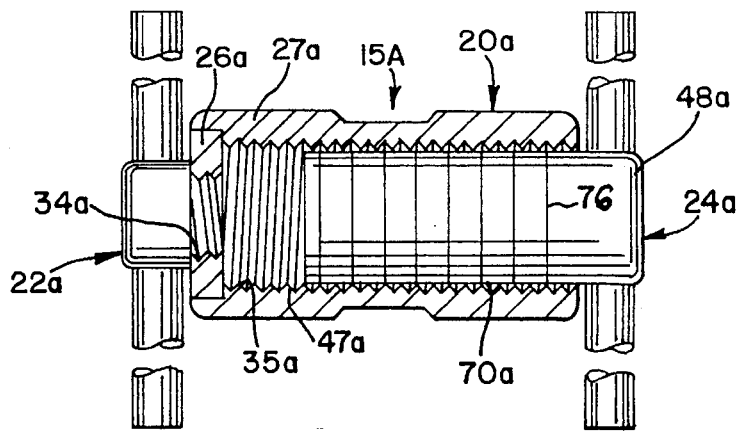
FIG. 10 is a vertical sectional view of a further embodiment of the palatal expander of the present invention but showing the outer expansion member in full view and the expander in closed position.

Referring now to the drawings, and particularly to FIGS. 1 and 2, the palatal expander or expansion screw of the present invention is generally indicated by numeral 15 and illustrated in mounted position on the upper jaw or maxilla for producing a force between opposite sides of the jaw. As specifically shown in FIG. 2, the palatal expander 15 will be generally received in the palatal cavity 17 of the upper jaw and mounted at opposite ends to teeth of the upper jaw.

The palatal expander 15 includes generally a rotatable adjusting member 20, an inner expansion member or screw 22, and an outer expansion member or screw 24. As will be described below, rotation of the adjustable member 20 will cause movement of the opposing members 22 and 24 toward each other and away from each other depending upon the direction of rotation of the adjusting member.

The rotatable adjusting member 20 includes an inner sleeve 26 and an outer sleeve 27 interconnected at one end, as seen in FIG. 4. The inner sleeve is longer than the outer sleeve and at least partially telescopically received within the outer sleeve. The inner sleeve includes an outer radial flange 29 at one end that is matingly received by the outer sleeve 27. The outer sleeve includes an outer cylindrical surface 31 and an interior bore 32. The interior bore 32 mates with the periphery of the flange 29 of the inner sleeve and may be suitably welded thereto at 33. Thus, the inner and outer sleeves are concentrically arranged and spaced from each other to define an annular opening and connected together at one of their ends to define the adjustable member 20.

At one end of the inner sleeve 26 an internal threaded area 34 threadedly receives the inner expansion member 22. An external threaded portion 35 is provided at the other end of the inner sleeve for threadedly receiving the outer expansion member 24. The internal threads 34 on the internal sleeve 27 are positioned at one end of the sleeve, while the external threads 35 are positioned at the other end of the sleeve and outward of the corresponding end of the external sleeve 27. Threads 34 and 35 are of opposite hand.

The inner expansion member 22 includes a shank 37 having an external threaded area 38 that is threadedly engaged by the internal threads 34 of the inner sleeve 26. The outer end of the shank 37 includes a head 39 having a transverse opening or bore 40 for receiving a mounting wire 41. The head may have a plurality of openings and receive a plurality of wires, or be formed to receive other devices for attaching to the jaw. Preferably, the wire is secured in place on the head. The inner end of the shank 37 is swedged at 42 to prevent the inner expansion member from completely unscrewing from the adjustable member 20. The swedged area would bind at the inner end of the internal threads 34 to prevent further relative rotation of the adjustable member relative to the inner expansion screw and the outer expansion screw.

The outer expansion screw or member 24 is in the form of a hollow cylindrical member closed at one end and includes an outer smooth face 46. Member 24 is internally bored and tapped to provide an internal threaded area 47 which threadedly mates with the external threads 35 of the inner sleeve 26. The outer end of the outer expansion member 24 is closed and provided with a head 48 having a transversely extending opening or bore 49 for receiving a mounting wire 50. Similar to the head 39 of the inner expansion member, the head 48 of the outer expansion member may have a plurality of openings for receiving a plurality of wires, or be formed to receive other devices for attaching to the jaw. Preferably, the pitch of the threads on the inner sleeve 26, the inner expansion member 22, and the outer expansion member 24 is the same, thereby providing a uniform and smooth movement between the parts during rotation of the rotatable adjusting member 20. The thread pitch and arrangement of the threads is such also that two millimeters of expansion of the expander is produced during traverse of one millimeter of working thread as the adjustable member drives both expansion members simultaneously and the same distance. Thus, the expander of the invention includes a double telescopic screw arrangement where the expansion screws do not rotate but move linearly. Further, the threading arrangement provides two millimeters of expansion for every millimeter of thread length of the device. Thus, one millimeter of thread length on the adjusting member operatively produces two millimeters of expansion. While it is preferred the pitch at opposite ends of the inner sleeve is the same, it could be different if desired, which would result in moving the expansion members at different linear rates.

As seen particularly in FIG. 4, the outer expansion screw 24 will be telescopically received by the adjusting member 20 during most of the travel of the outer expansion screw over the inner sleeve of the adjusting member. Further, the exterior threads on the inner sleeve are of the opposite hand to the internal threads on the inner sleeve such that rotation of the adjustable member 20 will cause the inner and outer expansion members to move in opposite directions from each other during expansion and in opposite directions toward each other during contraction.

It will be appreciated that the palatal expander of the invention is custom fitted to a particular patient, and accordingly the orthodontist will make a determination as to how the mounting wires 41 and 50 are to be formed for mounting the appliance in the mouth of a particular patient. One form of mounting is illustrated in FIGS. 1 and 2, wherein the mounting wires 41 and 50 have been suitably bent at their opposite ends and respectively secured to bands 54 at one end and bands 55 at the other end. The bands 54 are in turn suitably cemented to teeth 56 on one side of the jaw, while the bands 55 are suitably cemented to teeth 57 on the other side of the jaw. Accordingly, adjustment of the expander by rotation of the adjustable member 20 will cause movement between the inner expansion member 22 and outer expansion member 24 either toward each other or away from each other depending upon the selected rotation of the adjusting member 20. It should be further appreciated that the mounting wires 41 and 50 may also be suitably embedded in acrylic plates which are suitably fitted to engage the teeth at opposite sides of the jaw as another method of mounting the expander in the mouth of a patient for producing expansion of the upper jaw. As seen in FIG. 4, there is telescopic overlap of the inner and outer expansion screws when the expander is in closed to substantially open conditions, thereby facilitating the compactness, and a relatively long expansion length.

It is also unique with the present invention to provide a system for adjusting the rotatable adjusting member 20 to provide fine adjustment of the palatal expander and also to avoid any hazard to the patient. This system includes forming a hex nut 60 on the exterior surface of the adjustable member 20 having a plurality of flat faces 61 arranged in hexagonal fashion. The hex nut 60 can then be engaged by a suitable wrench, as shown by the open-end wrench 64 in FIGS. 6 and 7, or the open-end wrench 65 in FIGS. 8 and 9. The wrench 64 includes a handle 66 having a hole 67 at one end for selectively receiving a length of string or the like and a nut-engaging head 68 at the other end. The nut-engaging head 68 includes opposed flat faces 69 sized to fit on the hex nut 60 of the adjustable member. The head 68 is rotatably offset 90 degrees from the flat of the handle 66, and the flat hex-engaging faces 69 are offset by an angle 70 from the longitudinal axis of the handle 66. Preferably, this angle is 15 degrees which facilitates the insertion of the wrench into the mouth to easily engage with the hex nut 60. The handle 66 is preferably at least three inches long so that it can easily be manipulated from the front of the patient and also to avoid possible loss of the wrench in the patient's mouth where the wrench could be swallowed. While the expander is illustrated with a hex nut having six wrench-engaging faces, it may be appreciated that a nut with any number of wrench-engaging faces may be provided. Moreover, the wrench face may include a plurality of holes or axial recesses for receiving a spanner wrench.

The wrench 65 differs from the wrench 64 only in that it includes a handle 72 which is not angularly offset from the head 73. The head 73 includes flat faces 74 which are angularly offset from the longitudinal axis of the handle 72 by an angle 73a in the same manner as the offset in the wrench 64. Preferably, this offset angle is 15 degrees, although it may be whatever offset is believed to be the most practical for operation of the wrench relative to the hex nut on the adjusting member. Because of the hex nut and wrench arrangement, the nut may be turned as little as one-twelfth of a revolution, thereby enabling fine adjustment.

Accordingly, it will be appreciated that the palatal expander of the present invention includes a relatively small number of parts which can be economically made and assembled and which produces a compact expansion device that can be efficiently adjusted during the treatment of a patient for obtaining the optimum expansion of a patient's upper jaw.

Referring now to FIGS. 10 to 13, a further embodiment of the palatal expander or expansion screw of the present invention is shown and generally indicated by numeral 15A. Like palatal expander 15, palatal expander 15A will be generally received in the palatal cavity of the upper jaw and mounted at opposite ends to teeth of the upper jaw. The palatal expander 15A generally includes a rotatable adjusting member 20a, an inner expansion member or screw 22a, and an outer expansion member or screw 24a. The rotation of the adjustable member 20a will cause movement of the opposing members 22a and 24a toward each other or away from each other depending upon the direction of rotation.

The rotatable adjusting member 20a includes an inner sleeve 26a and an outer sleeve 27a interconnected at one end in the same fashion described above for interconnecting sleeves 26 and 27. The inner sleeve 26a has a shorter length than sleeve 26 and does not extend out from outer sleeve 27a. Sleeve 26a is telescopically received within the outer sleeve 27a, and spaced from the outer sleeve to define an annular opening.

Figure 11:
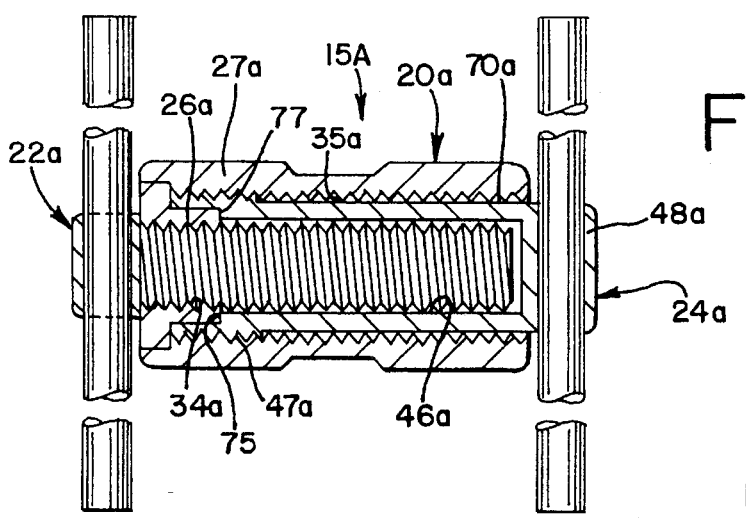
FIG. 11 is a vertical sectional view like FIG. 10, but also showing the outer expansion member in section.

The inner sleeve 26a has an internal or interior threaded area 34a which threadedly receives inner expansion member 22a. However, unlike sleeve 26, sleeve 26a does not have an exterior screw-threaded surface. Rather, the outer sleeve 27a has an internal or interior threaded area 35a, extending from the end connected to the inner sleeve 26a to the opposite end of the outer sleeve 27a, for threadedly receiving the outer expansion member 24a. Threads 34a and 35a are of opposite hand. The inner expansion member 22a is identical to the inner expansion member 22 and threadedly engages the internal threads 34a of the inner sleeve 26a. Similar to member 24, the outer expansion member 24a is in the form of a hollow cylindrical member closed at one end and is internally bored with a head 48a identical to head 48 of outer expansion member 24. The outer expansion member 24a includes an inner or interior smooth face 46a. The end opposite the head 48a of the outer surface 70a of the outer expansion member 24a is provided with an external or exterior threaded area 47a which threadedly mates with the internal threads 35a of the outer sleeve 27a. As best seen in FIG. 11, the outer expansion member includes a shoulder or lip 75 which is adapted to engage shoulder or stop 77 of the inner sleeve 26a, thereby preventing further inward movement of the outer expansion member 24a.

Figure 12:
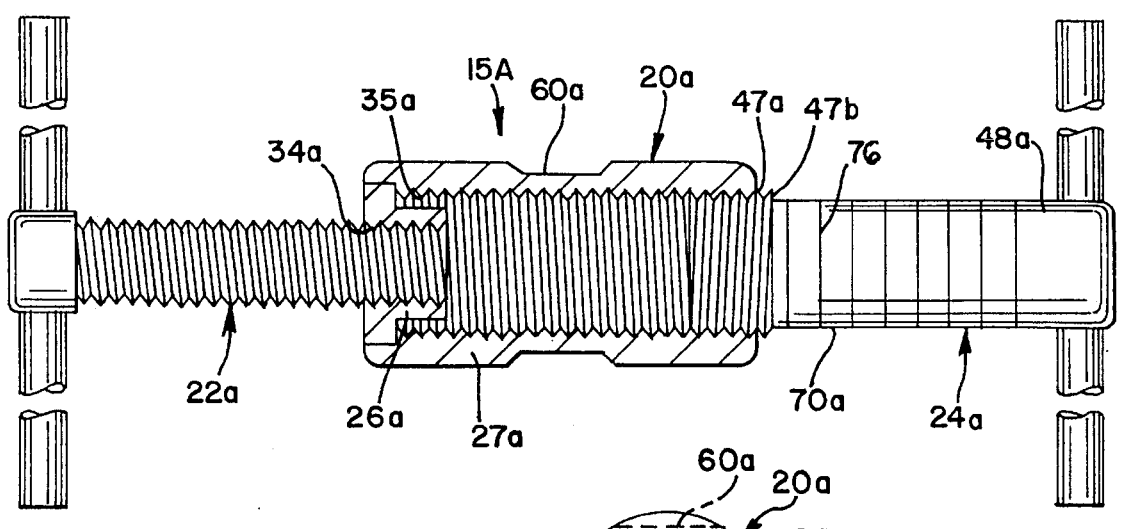
FIG. 12 is a vertical sectional view of the palatal expander of FIG. 10 showing the expander in open position.
Figure 13:
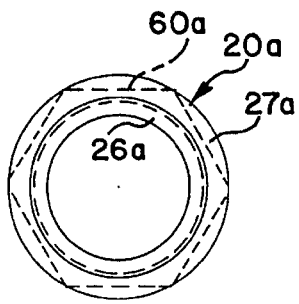
FIG. 13 is an end view of the adjusting member of the embodiment of FIG. 10, looking at the end receiving the inner expansion member.

The exterior surface 70a of the outer expansion member 24a is smooth and further includes markings 76 preferably in the form of grooves spaced apart to indicate to the user the amount of expansion, as best seen in FIG. 12. In the preferred embodiment, every marking indicates two millimeters of expansion in relation to the end of the outer sleeve, but it should be appreciated that the spacing of the markings could vary. It should also be appreciated that indicia other than grooves could be used to measure expansion. When the shoulder 47b of threaded area 47a on the outer expansion member appears as in FIG. 12, it indicates the limit of expansion of the palatal expander 15A.

Preferably, the pitch of the threads on the inner sleeve 26a, the inner expansion member 22a, the outer sleeve 27a, and the outer expansion member 24a is the same, thereby providing a uniform and smooth movement between the parts during rotation of the rotatable adjusting member 20a. Similar to palatal expander 15, the thread pitch and arrangement of the threads in palatal expander 15a is such that two millimeters of expansion of the expander 15a is produced during transverse of one millimeter of working thread as the adjustable member 20a drives both expansion members simultaneously in opposite directions and the same distance. Accordingly, the palatal expander 15a also includes a double telescopic screw arrangement where the expansion screws do not rotate because they are connected by wires to the arch but move linearly as in expander 15. Otherwise, the operation and construction of expander 15a is identical to expander 15 including the method of rotating the rotatable adjusting member 20a by a wrench applied to the hex nut 60a.

It will be understood that modifications and variations may be effected without departing from the scope of the novel concepts of the present invention, but it is understood that this application is to be limited only by the scope of the appended claims.

The invention is hereby claimed as follows:

1. An orthodontic expansion screw for producing an expansion force between opposite sides of the upper jaw comprising a first threaded member adapted to be secured to one side of the jaw, a second threaded member adapted to be secured to the other side of the jaw, and a rotatable adjusting member threadedly connected to said first and second threaded members such that said first and second threaded members are telescopically received by said adjusting member in overlapping relation and telescopically received with each other when the screw is substantially closed, whereby selective rotation of said adjusting member causes the first and second threaded members to move away from or toward each other.

2. The orthodontic expansion screw of claim 1, wherein hex nut faces are provided on the adjusting member for receiving a wrench for adjusting the expansion of said screw.

3. The orthodontic expansion screw of claim 1, wherein said rotatable adjusting member includes an outer sleeve and an inner sleeve fixedly connected to the outer sleeve at one end and disposed at least partially within the outer sleeve.

4. The orthodontic expansion screw of claim 3, wherein said inner sleeve has interior and exterior screw-threaded surfaces, said exterior threaded surface adapted to threadedly receive one of said threaded members and said interior threaded surface adapted to threadedly receive the other of said threaded members.

5. The orthodontic expansion screw of claim 3, wherein said outer sleeve has an interior screw-threaded surface adapted to threadedly receive one of said threaded members and said inner sleeve has an interior screw-threaded surface adapted to threadedly receive the other of said threaded members.

6. The orthodontic expansion screw of claim 5, wherein one of said threaded members includes means for indicating the amount of expansion of the screw as the adjusting member is rotated.

7. The orthodontic expansion screw of claim 6, wherein the threaded member having the indicating means includes a smooth exterior surface having incrementally spaced apart markings.

8. The orthodontic expansion screw of claim 7, wherein said markings are annular grooves.

9. A palatal expander for expanding the upper jaw comprising
   a rotatable adjusting member having an outer sleeve and an inner sleeve fixedly connected to the outer sleeve and disposed at least partially within the outer sleeve, the inner sleeve having an exterior screw-threaded surface and an interior screw-threaded surface;
   a first expansion member threadedly received by the exterior screw-threaded surface of the inner sleeve and telescopically received by said outer sleeve; and
   a second expansion member threadedly received by the interior screw-threaded surface of the inner sleeve and telescopically received by the inner sleeve,
   said members being arranged in overlapping relationship and whereby selective rotation of said adjusting member causes the first and second expansion members to move away from or toward each other.

10. The palatal expander of claim 9, wherein said adjusting member includes wrench-engaging faces on its outer surface.

11. The palatal expander of claim 9, wherein said first expansion member includes a head having an opening or openings for receiving a mounting wire or wires or other attachment means.

12. The palatal expander of claim 11, wherein the wire-receiving opening extends transverse the longitudinal axis of said first member.

13. The palatal expander of claim 9, wherein said second expansion member includes a head having an opening or openings for receiving a mounting wire or wires or other attachment means.

14. The palatal expander of claim 13, wherein the wire-receiving opening extends transverse the longitudinal axis of said second member.

15. The palatal expander of claim 9, wherein said threads on said exterior and interior surfaces of the inner sleeve have the same thread pitch.

16. The palatal expander of claim 15, wherein the rate of movement of the first expansion member and the second expansion member are consistent as the adjusting member is rotated.

17. The palatal expander of claim 9, wherein the threading of the members is such that two millimeters of expansion is produced for every millimeter of working thread.

18. The palatal expander of claim 9, wherein the threading of the interior screw-threaded surface of the rotatable adjusting member is opposite to the threading of the exterior screw-threaded surface thereof.

19. A palatal expander mountable between opposed sides of the upper jaw for expanding the jaw, said expander comprising,
   a rotatable adjusting member having an outer sleeve and an inner sleeve disposed at least partially within the outer sleeve, said sleeves being connected together at one end and sized to define an annular slot open at one end, said inner sleeve having interior threads at the end where connected to the outer sleeve and exterior threads at the other end which extends beyond the outer sleeve, a first expansion member threadedly received by the interior threads of said inner sleeve to be telescopically received within said inner sleeve and having means for attaching to one side of the jaw, a second expansion member threadedly received by the exterior threads of said inner sleeve and having means for attaching to the other side of said jaw, said second expansion member being tubular and sized to be telescopically received in said annular slot, whereby selective rotation of said adjusting member causes both expansion members to move away from or toward each other.

20. The palatal expander of claim 19, which further includes wrench-engaging means on said adjusting member for receiving a wrench to facilitate rotation of said adjusting member.

21. The palatal expander of claim 20, wherein said wrench-engaging means is a hex nut.

22. The palatal expander of claim 19, wherein the threads on opposite ends of the inner sleeve of the adjusting member are of opposite hand.

23. A palatal expander for expanding the upper jaw comprising, a rotatable adjusting member having an outer sleeve and an inner sleeve fixedly connected to the outer sleeve and disposed at least partially within the outer sleeve, the outer sleeve having an interior screw-threaded surface, the inner sleeve having an interior screw-threaded surface;

a first expansion member threadedly received by the interior screw-threaded surface of the outer sleeve and telescopically received by said outer sleeve; and a second expansion member threadedly received by the interior screw-threaded surface of the inner sleeve and telescopically received by the inner sleeve, said members being arranged in overlapping relationship and whereby selective rotation of said adjusting member causes the first and second expansion members to move away from or toward each other.

24. The palatal expander of claim 23, wherein the first expansion member includes a smooth outer surface having means thereon for indicating the amount of expansion of the expander as the adjusting member is rotated.

25. The palatal expander of claim 24, wherein said indicating means includes incrementally spaced apart markings on its outer surface whereby every marking indicates a predetermined amount of expansion.

26. The palatal expander of claim 25, wherein the markings are annular grooves.

27. An orthodontic expansion device for producing an expansion force between opposite sides of the upper jaw comprising: a first threaded member, a second threaded member, a rotatable adjusting member drivingly connected to said first and second threaded members for adjusting the positions of said members, and means for indicating the amount of expansion of the device as the adjusting member is rotated including spaced apart markings on a curved surface to enhance readability from any angle when the mouth is open, whereby selective rotation of said adjusting member causes the first and second threaded members to move away from or toward each other and the amount of expansion can be determined by the indicating means.

28. The combination of claim 27, wherein said markings are incrementally spaced apart and every marking indicates a predetermined amount of expansion.

29. The combination of claim 28, wherein the markings are metrically spaced apart.

30. The combination of claim 27, wherein said markings are incrementally spaced apart on one of said first or second threaded members, and said adjusting member coacts with said markings to measure the expansion.

31. The combination of claim 27, which further includes wrench-engaging means on said adjusting member for receiving a wrench to facilitate rotation of said adjusting member.

32. The combination of claim 31, wherein said wrench-engaging means is hexagonally shaped.

33. The combination of claim 32, wherein said threaded and adjusting members are arranged in overlappling relationship thereby providing a compact expansion device.

* * * * *